(12) United States Patent
Chen

(10) Patent No.: US 6,882,611 B2
(45) Date of Patent: Apr. 19, 2005

(54) METHOD AND APPARATUS FOR DEFECT DETECTION IN OPTICAL DISC DRIVES

(75) Inventor: Chih-Yuan Chen, Chang-Hua Hsien (TW)

(73) Assignee: Media Tek Inc., Hsin-Chu (TW)

( * ) Notice: Subject to any disclaimer, the term of this patent is extended or adjusted under 35 U.S.C. 154(b) by 346 days.

(21) Appl. No.: 10/064,044

(22) Filed: Jun. 4, 2002

(65) Prior Publication Data
US 2003/0223335 A1 Dec. 4, 2003

(51) Int. Cl.[7] .................................................. G11B 7/00
(52) U.S. Cl. .................................. 369/53.15; 369/53.17
(58) Field of Search ........................... 369/53.12, 53.13, 369/53.15, 53.17, 53.32

(56) References Cited

U.S. PATENT DOCUMENTS

| | | | |
|---|---|---|---|
| 5,377,054 A | * | 12/1994 | Yamaguchi et al. .......... 360/39 |
| 5,818,804 A | | 10/1998 | Ando et al. |
| 5,841,751 A | | 11/1998 | Komazaki et al. |
| 6,084,836 A | | 7/2000 | Kamiyama |
| 6,172,953 B1 | | 1/2001 | Kamiyama |

* cited by examiner

Primary Examiner—Nabil Hindi
(74) Attorney, Agent, or Firm—Winston Hsu

(57) ABSTRACT

A defect detection method is used to generate a disc defect signal while recording or reproducing information recorded onto an optical disc. The method compares the difference between a reflected light intensity signal (SBAD) and a low-pass filtered SBAD with a predetermined level. A defect signal is generated during a period when the difference exceeds a predetermined value. The defect signal opens a switch to hold the low-passed signal of the SBAD and disconnects the low-pass filter from the SBAD at the moment a defect signal occurs. The held value of the low-passed signal effectively replaces the low-passed signal until the difference between the SBAD and held low-passed signal returns to within the predetermined limits, which re-closes the switch re-connecting the low-pass filter to the SBAD.

16 Claims, 5 Drawing Sheets

METHOD AND APPARATUS FOR DEFECT DETECTION IN OPTICAL DISC DRIVES

BACKGROUND OF INVENTION

1. Field of the Invention

The present invention relates to disc defect detection in data reproduction systems. More specifically, a method and an apparatus for accurately generating disc defect signals during data recording and/or data reproduction in an optical disc system is disclosed.

2. Description of the Prior Art

In data reproduction systems, such as a CD-RW drive and a DVD-RW drive, it is important to know which areas of a disc are unusable due to defects. In an information recording system that supports defect management, a defect circuit must be able to generate accurate defect signals for the correct duration of the defect during data recording and/or data reproduction.

It is well known that an area of a disc containing a defect reflects the light differently than other areas of the same disc. A conventional defect detection system uses this variation in a reflected light intensity signal to determine the presence or absence of a disc defect. The general prior art method of determining disc defects involves comparing the currently reflected light intensity signal with an average of the same reflected light intensity signal. If the difference between the reflected light intensity signal and an averaged reflected light intensity signal value over a predetermined time period is larger than a preset threshold, a defect signal is generated.

FIG. 1 is a defect detection circuit 20 according to a prior art. The defect detection circuit 20 comprises a low-pass filter 24, a subtractor 28, two comparators 22a and 22b, and an OR operator 26. A reflected light intensity signal (SBAD) is split with one portion sent through the low-pass filter 24 creating a new, low-frequency signal (SBAD_LPF). The subtractor 28 subtracts the SBAD_LPF from the original SBAD and transmits the result to the two comparators 22a and 22b. The comparator 22a outputs "true" only if the result is larger than a preset positive threshold (DFTH_P). Similarly, the comparator 22b outputs "true" only if the result is smaller than a preset negative threshold (DFTH_N). If the OR operator 26 receives a "true" value from either of the comparators 22a or 22b, a disc defect signal is generated.

FIG. 2 shows the various signals throughout the detection process. FIG. 2 illustrates a defect signal generated by the comparator 22b based on a result smaller than the preset negative threshold (DFTH_N). However, it should be noted that a signal based on exceeding the DFTH_P would function similarly. In practice, the use of one positive threshold (DFTH_P) and one negative threshold (DFTH_N) commonly, but not necessarily, functions the same as taking the absolute value of the result from the subtractor 28 and having only one threshold.

The left side of FIG. 2 shows signals generated over an area of the disc containing no defects. Therefore, the incoming SBAD and the low-passed SBAD_LPF are approximately equal. When a disc defect occurs, the intensity of the SBAD changes far faster than the SBAD_LPF, creating a divergence that quickly exceeds the preset negative threshold (DFTH_N), causing a defect signal to be generated. When the area of the disc containing the defect has passed and another area of the disc is again reflecting the sub-beams, the SBAD returns to a normal value. Now, the difference between the SBAD and the SBAD_LPF is again less than the threshold, resulting in a defect signal no longer being generated.

The main benefit of the above defect detection method is that a disc defect can be also detected during recording with the SBAD signal by sampling the sub-beams of the optical pickup in land recording. However, the above defect detection method fails and generates inaccurate defect signals during a long defect as shown in FIG. 3. The main reason is that the average of the SBAD gradually shadows the SBAD when the defect period is relatively longer than the time constant of the low-passed filter. The defect signal shown in FIG. 3 starts at point T1 and erroneously ends at point T2 because of the difference between the SBAD and the averaged SBAD_LPF is smaller than the preset threshold. Additionally, an erroneous defect signal is generated from point T3 to point T4 during which the SBAD_LPF cannot return to the normal SBAD level rapidly enough and the difference between SBAD and SBAD_LPF is overly large, again triggering the defect signal. The prior art generated defect signal can provide false information about the length of the defect, which may cause failure in disc defect management.

SUMMARY OF INVENTION

It is therefore an objective of the invention to provide a method that can supply an accurate defect signal regardless of the length of the disc defect.

The method of defect detection according to one embodiment includes obtaining a low-frequency signal from a reflected light intensity signal and comparing the difference between the low-frequency signal and the reflected light intensity signal with a predetermined threshold. When the comparison reveals a disc defect, the low-frequency signal is held for use in future comparisons. When a defect is no longer indicated, the held low-frequency signal is no longer held.

According to one embodiment, the method begins with a reflected light intensity signal (SBAD) that is the sum of reflected sub-beams of an optical pickup. A low-frequency signal (SBAD_LPF) is obtained from the SBAD using a low-pass filter. A difference signal that is the difference between the average of the SBAD over a predetermined time period and the SBAD_LPF is found, and the difference signal is compared with a predetermined threshold that defines a range indicating whether a defect signal should or should not be issued. When the difference exceeds the predefined threshold, the defect signal is issued and a switch is opened, holding the current SBAD_LPF. The held value of the SBAD_LPF is used to obtain the difference signal until the SBAD again falls within the predetermined range and a defect signal is no longer issued, which in turn, closes the switch, and re-allows the generation of a new SBAD_LPF.

It is an advantage of the invention that an accurate defect detection signal, regardless of the length of the disc defect, can be generated, improving the art of disc defect management.

These and other objectives of the invention will no doubt become obvious to those of ordinary skill in the art after reading the following detailed description of the preferred embodiment, which is illustrated in the various figures and drawings.

DETAILED DESCRIPTION

Figure 5:
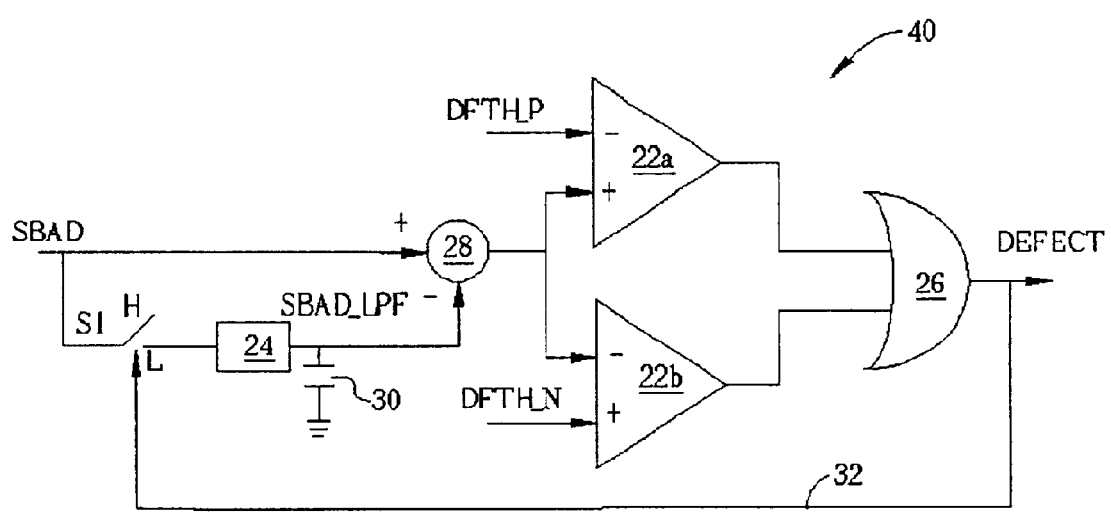
FIG. 5 is a diagram of a disc defect detection circuit according to the present invention.

A present invention defect detection circuit 40 is shown in FIG. 5. The defect detection circuit 40 comprises the OR operator 26, the first comparator 22a, the second comparator 22b, the subtractor 28, and the low-pass filter 24.

When no defect signal is generated, the defect detection circuit 40 operates similarly to the prior art. The sum of the sub-beams reflected by the disc (SBAD) is sent to the subtractor 28 via two paths, one being a direct path, the second being routed through the low-pass filter 24 where the SBAD is converted into a low-frequency signal (C). The subtractor 28 subtracts the SBAD_LPF from the SBAD and provides a difference signal to each of the comparators 22a, and 22b. The comparator 22a compares the difference signal with a first predetermined value (DFTH_P) and outputs the result to one input of the OR operator 26. The comparator 22b compares the difference signal with a second predetermined value (DFTH_N) and outputs the result to another input of the OR operator 26. The OR operator 26 issues or does not issue a defect signal based on the inputs received. When the difference signal falls within a predetermined threshold, which is the range defined by the first predetermined value (DFTH_P) and the second predetermined value (DFTH_N), no defect signal is issued.

Unfortunately, most discs contain more or less defects. The comparators 22a and 22b combined with the predetermined values DFTH_P and DFTH_N are used to check if the variations of the difference signal falls within a predefined range. When the difference signal falls outside of the predefined range, a disc defect has been detected and a defect signal is issued. If the magnitudes of DFTH_P and DFTH_N are equal, the same result can be obtained by comparing the absolute value of the difference signal with a single predetermined value. However, the magnitudes of DFTH_P and DFTH_N do not necessarily have to be the same and the present invention teaches both variations.

The defect detection circuit 40 also comprises a capacitor 30 and a switch S1. The switch S1 controls whether the SBAD is sent to the low-pass filter 24 and is controlled by the defect signal. When the switch S1 is closed (position L) with no defect signal issued, the SBAD signal is routed in part through the low-pass filter 24 to the subtractor 28. When the switch S1 is opened (position H) due to the issuance of a defect signal, the SBAD signal can no longer flow through the low-pass filter 24. Therefore, the value of the low-passed signal (SBAD_LPF) that reaches the subtractor 28 is the SBAD_LPF held by the capacitor 30.

The switch S1 and capacitor 30 are important in this embodiment. Without the switch S1 and the capacitor 30, the defect detection circuit 40 would still function, but would not function properly if the period of the defect signal were longer than the time constant of the low-passed filter. If the SBAD_LPF is not held during the defect period, the continuous averaging of the SBAD in obtaining the SBAD_LPF results in the SBAD_LPF following the curve formed by the SBAD. The effect of the SBAD_LPF shadowing the SBAD can produce erroneous start and end points for defect signals. The shadowing effect is effectively eliminated in this embodiment by holding the SBAD_LPF constant with the switch S1 and the capacitor 30 as soon as a defect is detected. This held, stored and constant SBAD_LPF, associated with the most recent area of the disc that did not generate a defect signal, is used as a basis for the threshold range, until the SBAD again falls within the range and a new SBAD_LPF can be properly generated.

Therefore, a defect signal is issued when a difference of the SBAD_LPF and the SBAD is greater than a predetermined value. Additionally, once a defect signal has been generated which opens the switch and holds the SBAD_LPF, a defect signal continues to be issued as long as the difference between the held SBAD_LPF and the SBAD remains greater than the predetermined value. When the difference between the held SBAD_LPF and the SBAD is no longer greater than the predetermined value, the switch is closed, reconnecting the reflected light intensity signal with the low-pass filter to generate a new SBAD_LPF.

Figure 1:
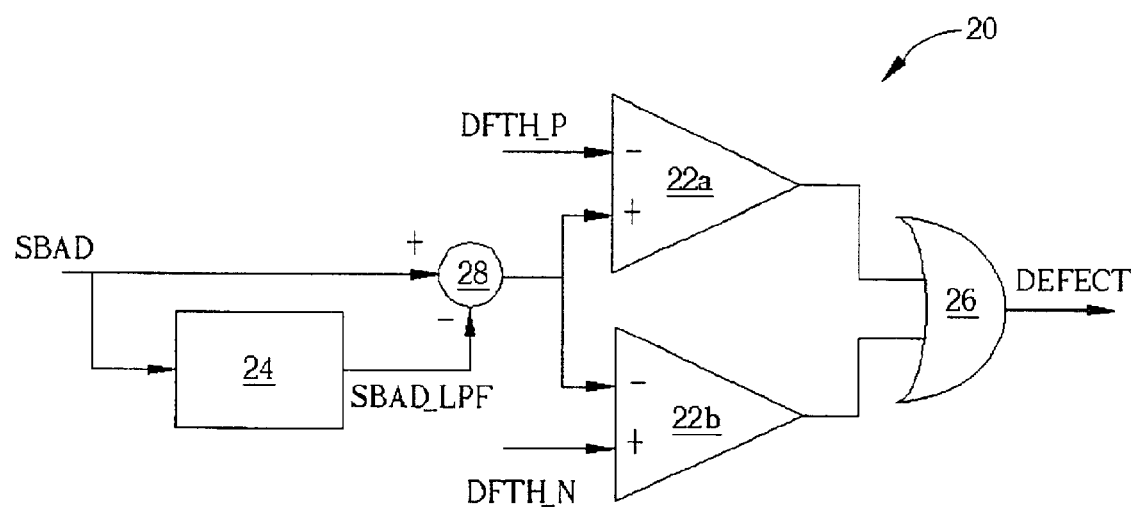
FIG. 1 is a diagram of a disc defect detection circuit according to a prior art.
Figure 2:
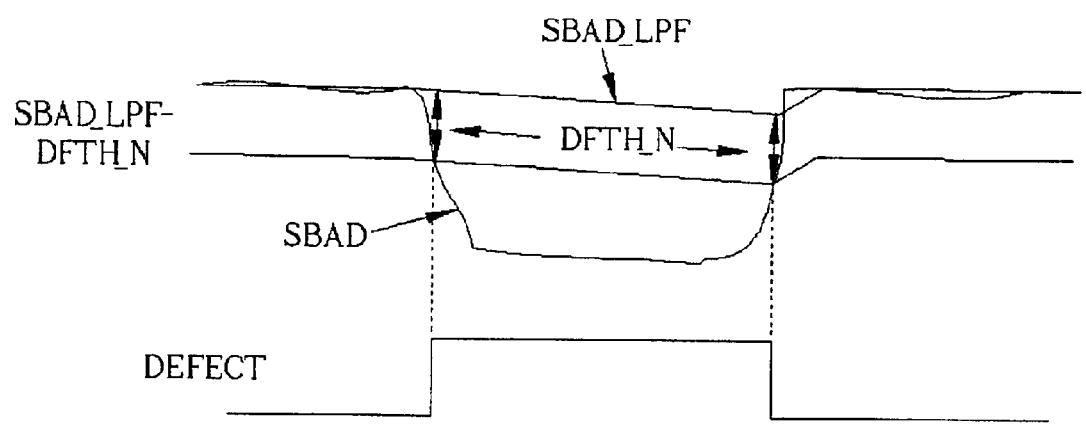
FIG. 2 is a chart of signals generated by the disc defect detection circuit of FIG. 1.
Figure 3:
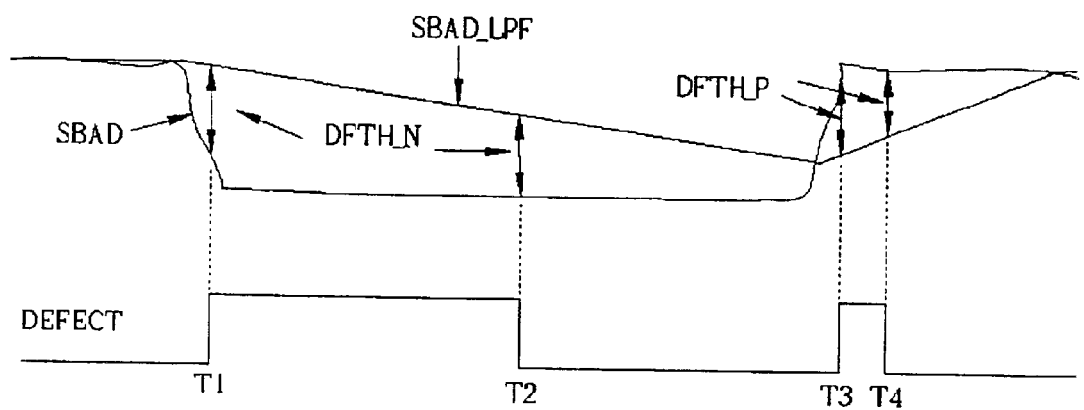
FIG. 3 is another chart of signals generated by the disc defect detection circuit of FIG. 1.
Figure 4:
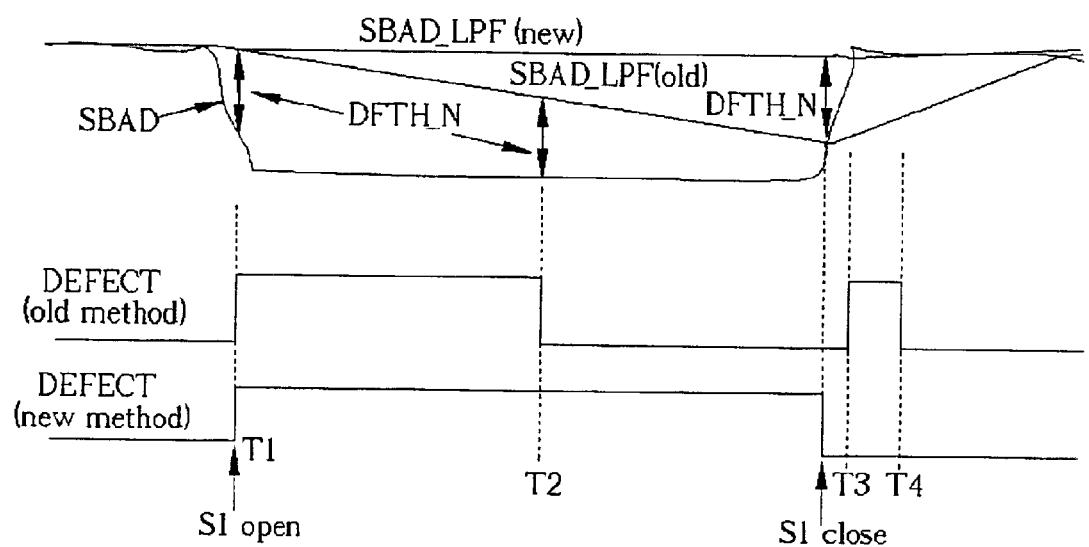
FIG. 4 is a comparison of signals generated by the disc defect detection circuit of FIG. 1 and the present invention.

In contrast to the prior art, the present invention clearly and distinctly shows an advantage by selectively switching between the held SBAD_LPF and generating a new one. Please refer to the comparison chart in FIG. 4. FIG. 4 shows the chart of FIG. 3 overlaid with the new signals generated by the present invention. Holding the SBAD_LPF constant during the period of a defect avoids the erroneous signals at T2, T3, and T4 because the shadowing effect has been avoided. The ability to hold the SBAD_LPF constant during the period of a defect allows the generation of accurate defect signals regardless of the length of the defect, permitting a more complete and accurate disc defect management system.

Those skilled in the art will readily observe that numerous modifications and alterations of the method may be made while retaining the teachings of the invention. Accordingly, the above disclosure should be construed as limited only by the metes and bounds of the appended claims.

What is claimed is:

1. A method of detecting disk defects in an optical disc for an optical disc drive including an optical pickup, the method comprising the steps of:
   emitting light from the optical pickup onto the optical disc and obtaining reflected sub-beams;
   generating a reflected light intensity signal based on the reflected sub-beams;
   obtaining a low-frequency signal from the reflected light intensity signal;
   holding the low-frequency signal when a difference between the reflected light intensity signal and the low-frequency signal is greater than a predetermined value;
   generating a defect signal when a difference between the reflected light intensity signal and the held low-frequency signal is greater than the predetermined value; and
   holding the held low-frequency signal substantially constant for the duration of the generated defect signal.

2. The method of claim 1 wherein the low-frequency signal is held by a capacitor.

3. The method of claim 1 wherein the reflected light intensity signal is generated by summing intensities of the reflected sub-beams.

4. The method of claim 1 wherein the low-frequency signal is the result of averaging the reflected light intensity signal over a time period defined by a predefined time constant.

5. The method of claim 1 wherein the low-frequency signal is obtained by passing the reflected light intensity signal through a low-pass filter.

6. The method of claim 1 wherein at least one comparator is used to compare the difference between the reflected light intensity signal and the held low-frequency signal with the predetermined value.

7. The method of claim 1 wherein when a difference between the reflected light intensity signal and the held low-frequency signal is within the predetermined value, the held low-frequency signal is no longer held.

8. A method of detecting disk defects in an optical disc for an optical disc drive including an optical pickup, the method comprising the steps of:

emitting light from the optical pickup onto the optical disc and obtaining reflected sub-beams;

generating a reflected light intensity signal based on the reflected sub-beams;

obtaining a low-frequency signal after the reflected light intensity signal is processed through a low-pass filter;

storing the low-frequency signal with a capacitor if a defect signal indicating existence of the disk defects appears based on a difference between the reflected light intensity signal and the low-frequency signal; and electrically disconnecting the capacitor from the reflected light intensity signal if the defect signal appears.

9. The method of claim 8 wherein the reflected light intensity signal is generated by summing intensities of the reflected sub-beams.

10. The method of claim 8 wherein the low-frequency signal is the result of averaging the reflected light intensity signal over a time period defined by a predefined time constant.

11. The method of claim 8 wherein the low-frequency signal is obtained by passing the reflected light intensity signal through a low-pass filter.

12. The method of claim 8 wherein at least one comparator is used to compare the difference between the reflected light intensity signal and the stored low-frequency signal with the predetermined value.

13. The method of claim 8 wherein when a difference between the reflected light intensity signal and the stored low-frequency signal is within the predetermined value, the stored low-frequency signal is no longer held.

14. An optical disc drive for use in a recording and/or data reproduction system utilizing a defect management system, the optical disc drive comprising:

an optical pickup capable of emitting light onto an optical disc and obtaining reflected sub-beams;

a low-pass filter for obtaining a low-frequency signal from a reflected light intensity signal, the reflected light intensity signal being based on the reflected sub-beams;

a holding circuit for holding the low-frequency signal when a difference between the reflected light intensity signal and the low-frequency signal is greater than a predetermined value; and a switch electrically disconnecting the low-pass filter from the reflected light intensity signal when a difference between the reflected light intensity signal and the low-frequency signal is greater then the predetermined value.

15. The optical disc drive of claim 14 further comprising a subtractor for generating the difference between the reflected light intensity signal and the low-frequency signal.

16. The method of claim 2 further comprising electrically disconnecting the capacitor from the reflected light intensity signal for the duration of the generated defect signal.

* * * * *